(12) United States Patent
Hayeck et al.

(10) Patent No.: US 7,229,445 B2
(45) Date of Patent: Jun. 12, 2007

(54) BONE PLATE WITH BLADED PORTION

(75) Inventors: Garry Hayeck, Ithaca, NY (US); René Haag, Berwyn, PA (US); Henry Kim, Media, PA (US); Mark P. Grady, Jr., West Chester, PA (US)

(73) Assignee: Synthes (USA), West Chester, PA (US)

( * ) Notice: Subject to any disclaimer, the term of this patent is extended or adjusted under 35 U.S.C. 154(b) by 0 days.

(21) Appl. No.: 10/874,097

(22) Filed: Jun. 21, 2004

(65) Prior Publication Data

US 2006/0004361 A1    Jan. 5, 2006

(51) Int. Cl.
    *A61B 17/80* (2006.01)
(52) U.S. Cl. ........................................ 606/70
(58) Field of Classification Search ............ 606/69–72
    See application file for complete search history.

(56) References Cited

U.S. PATENT DOCUMENTS

| | | | |
|---|---|---|---|
| 2,414,882 A | 1/1947 | Longfellow | |
| 2,443,363 A | 6/1948 | Townsend et al. | |
| 2,496,126 A | 1/1950 | Haboush | |
| 2,526,959 A | 10/1950 | Lorenzo | |
| 2,612,159 A | 9/1952 | Collison | |
| 2,627,855 A | 2/1953 | Price | |
| 2,699,774 A | 1/1955 | Livingston | |
| 2,772,676 A | 12/1956 | Pohl | |
| 2,801,631 A | 8/1957 | Charnley | |
| 3,025,853 A | 3/1962 | Mason | |
| 3,374,786 A | 3/1968 | Callender | |
| 3,489,143 A | 1/1970 | Halloran | |
| 3,552,389 A | 1/1971 | Allgower et al. | |
| 3,561,437 A | 2/1971 | Orlich | |
| 3,577,601 A | 5/1971 | Mariani et al. | |
| 3,668,972 A | 6/1972 | Allgower et al. | |

(Continued)

FOREIGN PATENT DOCUMENTS

CH    611147    5/1979

(Continued)

OTHER PUBLICATIONS

ACE Symmetry™ Titanium Upper Extremity Plates, Ace Medical Company.

*Primary Examiner*—Eduardo C. Robert
*Assistant Examiner*—Richard Shaffer
(74) *Attorney, Agent, or Firm*—Jones Day

(57) ABSTRACT

A bone plate for fixation of a fractured bone includes a first portion having a first longitudinal axis and a second portion having a second longitudinal axis. The second portion is angled with respect to the first portion. The first portion has at least one hole for receiving a bone anchor having a shaft. The hole has a first hole portion defining a first central axis substantially perpendicular to a lower surface of the first portion and configured to receive the bone anchor. The hole includes a second hole portion overlapping and in communication with the first hole portion from upper to lower surface defining a second central axis substantially angled with respect to the first central axis, and configured to receive the bone anchor such that the shaft is substantially angled with respect to the second portion of the bone plate so as to form a truss.

32 Claims, 10 Drawing Sheets

U.S. PATENT DOCUMENTS

| | | | |
|---|---|---|---|
| 3,695,259 A | 10/1972 | Yost | |
| 3,716,050 A | 2/1973 | Johnston | |
| 3,779,240 A | 12/1973 | Kondo | |
| 3,782,374 A | 1/1974 | Fischer | |
| 3,824,995 A | 7/1974 | Getscher et al. | |
| 3,842,825 A | 10/1974 | Wagner | |
| RE28,841 E | 6/1976 | Allgower et al. | |
| 3,996,931 A | 12/1976 | Callender, Jr. | |
| 4,009,712 A | 3/1977 | Burstein et al. | |
| 4,040,129 A | 8/1977 | Steinemann et al. | |
| 4,095,591 A | 6/1978 | Graham, Jr. et al. | |
| 4,120,298 A | 10/1978 | Fixel | |
| 4,172,452 A | 10/1979 | Forte et al. | |
| 4,219,015 A | 8/1980 | Steinemann | |
| 4,236,512 A | 12/1980 | Aginsky | |
| 4,269,180 A | 5/1981 | Dall et al. | |
| 4,379,451 A | 4/1983 | Getscher | |
| 4,408,601 A | 10/1983 | Wenk | |
| 4,438,762 A | 3/1984 | Kyle | |
| 4,454,876 A | 6/1984 | Mears | |
| RE31,628 E | 7/1984 | Allgower et al. | |
| 4,484,570 A | 11/1984 | Sutter et al. | |
| 4,488,543 A | 12/1984 | Tornier | |
| 4,493,317 A | 1/1985 | Klaue | |
| 4,494,535 A | 1/1985 | Haig | |
| 4,513,744 A | 4/1985 | Klaue | |
| 4,565,193 A | 1/1986 | Streli | |
| 4,612,920 A | 9/1986 | Lower | |
| 4,616,638 A | 10/1986 | Griggs | |
| 4,617,922 A | 10/1986 | Griggs | |
| 4,621,629 A | 11/1986 | Koeneman | |
| 4,628,923 A | 12/1986 | Medoff | |
| 4,651,724 A | 3/1987 | Berentey et al. | |
| 4,657,001 A | 4/1987 | Fixel | |
| 4,776,329 A | 10/1988 | Treharne | |
| 4,776,330 A | 10/1988 | Chapman et al. | |
| 4,791,918 A | 12/1988 | Von Hasselbach | |
| 4,795,473 A | 1/1989 | Grimes | |
| 4,800,874 A | 1/1989 | David et al. | |
| 4,838,252 A | 6/1989 | Klaue | |
| 4,848,328 A | 7/1989 | Laboureau et al. | |
| 4,867,144 A | 9/1989 | Karas et al. | |
| 4,903,691 A | 2/1990 | Heinl | |
| 4,905,680 A | 3/1990 | Tunc | |
| 4,927,421 A | 5/1990 | Goble et al. | |
| 4,936,844 A * | 6/1990 | Chandler et al. | 606/69 |
| 4,955,886 A | 9/1990 | Pawluk | |
| 4,957,496 A | 9/1990 | Schmidt | |
| 4,957,497 A | 9/1990 | Hoogland et al. | |
| 4,964,403 A | 10/1990 | Karás | |
| 4,966,599 A | 10/1990 | Pollock | |
| 4,973,332 A | 11/1990 | Kummer | |
| 4,973,333 A | 11/1990 | Treharne | |
| 4,988,350 A | 1/1991 | Herzberg | |
| 5,002,544 A | 3/1991 | Klaue et al. | |
| 5,006,120 A | 4/1991 | Carter | |
| 5,015,248 A | 5/1991 | Burstein et al. | |
| 5,041,114 A | 8/1991 | Chapman et al. | |
| 5,041,116 A | 8/1991 | Wilson | |
| 5,085,660 A | 2/1992 | Lin | |
| 5,087,260 A | 2/1992 | Fixel | |
| 5,108,399 A | 4/1992 | Eitenmuller et al. | |
| 5,108,449 A | 4/1992 | Gray | |
| 5,116,336 A | 5/1992 | Frigg | |
| 5,127,914 A | 7/1992 | Calderale et al. | |
| 5,129,901 A | 7/1992 | Decoste | |
| 5,151,103 A | 9/1992 | Tepic et al. | |
| 5,152,794 A | 10/1992 | Davidson | |
| 5,190,544 A | 3/1993 | Chapman et al. | |
| 5,197,966 A | 3/1993 | Sommerkamp | |
| 5,269,784 A | 12/1993 | Mast | |
| 5,275,601 A | 1/1994 | Gogolewski et al. | |
| 5,290,281 A | 3/1994 | Tschakaloff | |
| 5,300,074 A | 4/1994 | Frigg | |
| 5,304,180 A | 4/1994 | Slocum | |
| 5,324,290 A | 6/1994 | Zdeblick et al. | |
| 5,324,292 A | 6/1994 | Meyers | |
| 5,356,410 A | 10/1994 | Pennig | |
| 5,360,429 A | 11/1994 | Jeanson et al. | |
| 5,364,398 A | 11/1994 | Chapman et al. | |
| 5,364,399 A | 11/1994 | Lowery et al. | |
| 5,372,598 A | 12/1994 | Luhr et al. | |
| 5,376,126 A | 12/1994 | Lin | |
| 5,395,372 A | 3/1995 | Holt et al. | |
| 5,413,577 A | 5/1995 | Pollock | |
| 5,429,641 A | 7/1995 | Gotfried | |
| 5,458,654 A | 10/1995 | Tepic | |
| 5,462,547 A | 10/1995 | Weigum | |
| 5,484,439 A | 1/1996 | Olson et al. | |
| 5,514,138 A | 5/1996 | McCarthy | |
| 5,522,902 A | 6/1996 | Yuan et al. | |
| 5,586,985 A | 12/1996 | Putnam et al. | |
| 5,591,168 A | 1/1997 | Judet et al. | |
| 5,601,553 A | 2/1997 | Trebing et al. | |
| 5,607,427 A | 3/1997 | Tschakaloff | |
| 5,647,872 A | 7/1997 | Gilbert et al. | |
| 5,658,339 A | 8/1997 | Tronzo et al. | |
| 5,662,655 A | 9/1997 | Laboureau et al. | |
| 5,674,222 A | 10/1997 | Berger et al. | |
| 5,676,667 A | 10/1997 | Hausman | |
| 5,681,311 A | 10/1997 | Foley et al. | |
| D385,963 S | 11/1997 | Hansson | |
| 5,693,055 A | 12/1997 | Zahiri et al. | |
| 5,702,396 A | 12/1997 | Hoenig et al. | |
| 5,702,399 A | 12/1997 | Kilpela et al. | |
| 5,709,682 A | 1/1998 | Medoff | |
| 5,709,686 A | 1/1998 | Talos et al. | |
| 5,718,704 A | 2/1998 | Medoff | |
| 5,718,705 A | 2/1998 | Sammarco | |
| 5,728,099 A | 3/1998 | Tellman et al. | |
| 5,733,287 A | 3/1998 | Tepic et al. | |
| 5,743,912 A | 4/1998 | Lahille et al. | |
| 5,749,872 A | 5/1998 | Kyle et al. | |
| 5,772,662 A | 6/1998 | Chapman et al. | |
| 5,779,706 A | 7/1998 | Tschakaloff | |
| 5,797,916 A | 8/1998 | McDowell | |
| 5,800,553 A | 9/1998 | Albrektsson et al. | |
| 5,810,821 A | 9/1998 | Vandewalle | |
| 5,810,822 A | 9/1998 | Mortier | |
| 5,810,823 A | 9/1998 | Klaue et al. | |
| 5,853,413 A | 12/1998 | Carter et al. | |
| 5,921,988 A | 7/1999 | Legrand | |
| 5,931,839 A | 8/1999 | Medoff | |
| 5,938,664 A | 8/1999 | Winquist et al. | |
| 5,968,046 A | 10/1999 | Castleman | |
| 5,968,047 A | 10/1999 | Reed | |
| 5,973,223 A | 10/1999 | Tellman et al. | |
| 5,976,139 A | 11/1999 | Bramlet | |
| 6,007,535 A | 12/1999 | Rayhack et al. | |
| 6,022,352 A | 2/2000 | Vandewalle | |
| 6,066,141 A | 5/2000 | Dall et al. | |
| 6,096,040 A | 8/2000 | Esser | |
| 6,113,603 A | 9/2000 | Medoff | |
| 6,129,728 A | 10/2000 | Schumacher et al. | |
| 6,152,927 A | 11/2000 | Farris et al. | |
| 6,183,474 B1 | 2/2001 | Bramlet et al. | |
| 6,183,475 B1 | 2/2001 | Lester et al. | |
| 6,187,007 B1 | 2/2001 | Frigg et al. | |
| 6,206,881 B1 | 3/2001 | Frigg et al. | |
| 6,221,073 B1 | 4/2001 | Weiss et al. | |
| 6,221,075 B1 | 4/2001 | Tormala et al. | |
| D443,060 S | 5/2001 | Benirschke et al. | |
| 6,224,602 B1 | 5/2001 | Hayes | |
| 6,235,032 B1 | 5/2001 | Link | |

| Patent Number | Date | Inventor |
|---|---|---|
| 6,283,969 B1 | 9/2001 | Grusin et al. |
| 6,287,309 B1 | 9/2001 | Baccelli et al. |
| 6,290,703 B1 | 9/2001 | Ganem |
| 6,322,562 B1 | 11/2001 | Wolter |
| 6,325,803 B1 | 12/2001 | Schumacher et al. |
| 6,338,734 B1 | 1/2002 | Burke et al. |
| 6,348,052 B1 | 2/2002 | Sammarco |
| 6,350,265 B1 | 2/2002 | Blaustein et al. |
| 6,355,041 B1 | 3/2002 | Martin |
| 6,355,042 B2 | 3/2002 | Winquist et al. |
| 6,358,250 B1 | 3/2002 | Orbay |
| 6,364,882 B1 | 4/2002 | Orbay |
| 6,379,359 B1 | 4/2002 | Dahners |
| D458,374 S | 6/2002 | Bryant et al. |
| D458,683 S | 6/2002 | Bryant et al. |
| D458,684 S | 6/2002 | Bryant et al. |
| D458,996 S | 6/2002 | Bryant et al. |
| 6,440,131 B1 | 8/2002 | Haidukewych |
| 6,440,135 B2 | 8/2002 | Orbay et al. |
| D463,557 S | 9/2002 | Bryant et al. |
| D463,558 S | 9/2002 | Bryant et al. |
| D463,559 S | 9/2002 | Bryant et al. |
| 6,454,770 B1 | 9/2002 | Klaue |
| D464,136 S | 10/2002 | Bryant et al. |
| D464,731 S | 10/2002 | Bryant et al. |
| 6,468,278 B1 | 10/2002 | Muckter |
| 6,488,685 B1 | 12/2002 | Manderson |
| D469,532 S | 1/2003 | Bryant et al. |
| D469,533 S | 1/2003 | Bryant et al. |
| D469,534 S | 1/2003 | Bryant et al. |
| 6,503,252 B2 | 1/2003 | Hansson |
| 6,503,281 B1 | 1/2003 | Mallory |
| 6,508,819 B1 | 1/2003 | Orbay |
| D469,874 S | 2/2003 | Bryant et al. |
| D469,875 S | 2/2003 | Bryant et al. |
| D470,588 S | 2/2003 | Bryant et al. |
| 6,527,776 B1 | 3/2003 | Michelson |
| 6,533,789 B1 | 3/2003 | Hall, IV et al. |
| 6,602,256 B1 | 8/2003 | Hayes |
| 6,605,090 B1 | 8/2003 | Trieu et al. |
| D479,331 S | 9/2003 | Pike et al. |
| D480,141 S | 9/2003 | Benirschke et al. |
| 6,623,486 B1 | 9/2003 | Weaver et al. |
| 6,669,701 B2 | 12/2003 | Steiner et al. |
| 2001/0000186 A1 | 4/2001 | Bramlet et al. |
| 2001/0011172 A1 | 8/2001 | Orbay et al. |
| 2001/0012940 A1 | 8/2001 | Tunc |
| 2002/0013587 A1 | 1/2002 | Winquist et al. |
| 2002/0032446 A1 | 3/2002 | Orbay |
| 2002/0045901 A1 | 4/2002 | Wagner et al. |
| 2002/0049445 A1 | 4/2002 | Hall, IV et al. |
| 2002/0062127 A1 | 5/2002 | Schumacher et al. |
| 2002/0065516 A1 | 5/2002 | Winquist et al. |
| 2002/0128654 A1 | 9/2002 | Steger et al. |
| 2002/0143337 A1 | 10/2002 | Orbay et al. |
| 2002/0143338 A1 | 10/2002 | Orbay et al. |
| 2002/0156474 A1 | 10/2002 | Wack et al. |
| 2002/0183752 A1 | 12/2002 | Steiner et al. |
| 2002/0183753 A1 | 12/2002 | Manderson |
| 2003/0040748 A1 | 2/2003 | Aikins et al. |
| 2003/0055435 A1 | 3/2003 | Barrick |
| 2003/0060827 A1 | 3/2003 | Coughln |
| 2003/0083660 A1 | 5/2003 | Orbay |
| 2003/0083661 A1 | 5/2003 | Orbay et al. |
| 2003/0105461 A1 | 6/2003 | Putnam |
| 2003/0125738 A1 | 7/2003 | Khanna |
| 2003/0135212 A1 | 7/2003 | Chow |
| 2003/0135216 A1 | 7/2003 | Sevrain |
| 2005/0165400 A1* | 7/2005 | Fernandez .................. 606/69 |
| 2005/0171544 A1* | 8/2005 | Falkner, Jr. .................. 606/69 |

FOREIGN PATENT DOCUMENTS

| | | |
|---|---|---|
| CH | 670755 A5 | 7/1989 |
| DE | 37 22 852 A1 | 1/1989 |
| DE | 37 43 638 A1 | 7/1989 |
| DE | 42 01 531 A1 | 7/1993 |
| DE | 43 41 980 A | 6/1995 |
| DE | 43 43 117 A | 6/1995 |
| DE | 44 38 264 A1 | 3/1996 |
| DE | 196 36 733 A1 | 4/1997 |
| DE | 93 21 544 U1 | 10/1999 |
| DE | 100 15 734 A1 | 9/2001 |
| DE | 101 25 092 A1 | 12/2001 |
| EP | 0 180532 A1 | 5/1986 |
| EP | 0 274713 A1 | 12/1986 |
| EP | 0 207 884 A2 | 1/1987 |
| EP | 0 251583 A2 | 1/1988 |
| EP | 0 290138 A2 | 11/1988 |
| EP | 0 291632 A1 | 11/1988 |
| EP | 0 299160 A1 | 1/1989 |
| EP | 0 337288 A1 | 10/1989 |
| EP | 0 381 462 A3 | 8/1990 |
| EP | 0 381462 A2 | 8/1990 |
| EP | 0 382256 A1 | 8/1990 |
| EP | 0 471418 A1 | 2/1992 |
| EP | 0 532421 A1 | 3/1993 |
| EP | 0 546460 A1 | 6/1993 |
| EP | 0 649635 A1 | 4/1995 |
| EP | 0 668059 A1 | 8/1995 |
| EP | 0 760231 A1 | 3/1997 |
| EP | 1132052 A1 | 3/2000 |
| EP | 1132052 A3 | 3/2000 |
| EP | 1 468 655 A2 | 10/2004 |
| FR | 2233973 | 1/1975 |
| FR | 2405062 | 5/1979 |
| FR | 2405705 | 5/1979 |
| FR | 2405706 | 5/1979 |
| FR | 2496429 | 6/1982 |
| FR | 2606268 A1 | 5/1988 |
| FR | 2622431 A1 | 5/1989 |
| FR | 2650500 A1 | 2/1991 |
| FR | 2671966 A3 | 7/1992 |
| FR | 2677876 A1 | 12/1992 |
| FR | 2706763 A1 | 12/1994 |
| FR | 2757370 A1 | 6/1998 |
| GB | 2017502 A | 10/1979 |
| GB | 2090745 A | 7/1982 |
| GB | 2245498 A | 1/1992 |
| GB | 2257913 A | 1/1993 |
| JP | A-H02-121652 | 5/1990 |
| JP | 3158150 A | 7/1991 |
| JP | 4-138152 A | 5/1992 |
| JP | 6-125918 A | 5/1994 |
| JP | 6-245941 A | 9/1994 |
| JP | 8-98846 A | 4/1996 |
| JP | 8-126650 A | 5/1996 |
| JP | 8-257034 A | 10/1996 |
| JP | 8-266562 A | 10/1996 |
| JP | 9-108237 A | 4/1997 |
| JP | 11-76259 A | 3/1999 |
| JP | 11-276501 A | 10/1999 |
| JP | 11-299804 A | 11/1999 |
| JP | 11-318930 A | 11/1999 |
| JP | 2000-247 A | 1/2000 |
| JP | 2001-149379 A | 6/2001 |
| JP | 2001-161704 A | 6/2001 |
| JP | A-2002-95673 | 4/2002 |
| JP | 2002-345836 A | 12/2002 |
| JP | 2003-24344 A | 1/2003 |
| JP | 2003-38508 A | 2/2003 |
| JP | 2003-38509 A | 2/2003 |

| | | |
|---|---|---|
| SU | 1279626 A1 | 12/1986 |
| WO | WO 92/11819 A1 | 7/1992 |
| WO | WO 93/11714 A1 | 6/1993 |
| WO | WO 93/15678 A1 | 8/1993 |
| WO | WO 93/22982 A1 | 11/1993 |
| WO | WO 94/02073 A1 | 2/1994 |
| WO | WO 95/32674 A1 | 12/1995 |
| WO | WO 96/17556 A1 | 6/1996 |
| WO | WO 97/08999 A1 | 3/1997 |
| WO | WO 97/09000 | 3/1997 |
| WO | WO 98/02105 A1 | 1/1998 |
| WO | WO 98/05263 A1 | 2/1998 |
| WO | WO 0053110 | 9/2000 |
| WO | WO 0053111 | 9/2000 |
| WO | WO 02/071963 A1 | 9/2002 |
| WO | WO 03/022166 A1 | 3/2003 |
| WO | WO 03/028567 A1 | 4/2003 |

* cited by examiner

BONE PLATE WITH BLADED PORTION

FIELD OF THE INVENTION

The present invention relates generally to bone plates, and more specifically, to bone plates having a blade portion for the fixation of fractured bone, preferably long bones, including the femur and the tibia.

BACKGROUND OF THE INVENTION

A bone plate is a plate that is fastenable to the surface of a fractured bone to support and/or stabilize the fracture as the bone heals. Bone plates may be attached to the bone with bone screws that extend from the plate into the bone. In some examples, the head of the bone screw is locked to the plate (e.g., by threaded engagement between the screw head and the bone plate) and in other plates the head of the screw is free to angulate with respect to the plate, such that the screw may be placed in the bone at a surgeon-selected angle. In yet other examples, the screw head may cooperate with the bone plate to provide compression or distraction of the fracture (i.e., to push the bone fragments towards or away from one another).

When treating certain types of fractures, such as that of the proximal portion of the femur, there may be high stresses at the bone-screw and/or screw-plate interfaces. Several different types of bone plates have been developed to accommodate these high stresses. In one example, sometimes referred to as a "blade plate," the bone plate may have a blade-shaped portion that extends approximately perpendicularly to the plate, and extends into a channel formed in the bone through the fracture site. In another example, a lag screw may extend from a barrel portion of the plate and through the fracture site. However these additional structures, for example the blade-shaped portion, may require additional support due to the redistribution of stresses from the loads experienced throughout the remainder of the bone plate.

SUMMARY OF THE INVENTION

The present invention is directed to a bone plate for fixation of a fractured bone. In one embodiment, the bone plate may comprise a first plate portion having a first longitudinal axis, an upper surface and a lower surface and a second plate portion having a second longitudinal axis, an upper surface and a lower surface. The second plate portion may be angled with respect to the first plate portion such that the lower surface of the first plate portion and the lower surface of the second plate portion define a first included angle therebetween. The first portion of the bone plate may have at least one hole for receiving a bone anchor having a shaft, the hole having a first hole portion defining a first central axis substantially perpendicular to the lower surface and a second hole portion overlapping and in communication with the first hole portion from upper to lower surface and defining a second central axis substantially angled with respect to the first central axis. The second hole portion of the bone plate may be configured to receive a bone anchor such that the shaft of the bone anchor is not substantially perpendicular with respect to the first portion of the bone plate. The second portion of the bone plate may be a blade having a proximal end adjacent the first portion of the bone plate and a distal end, the blade configured and adapted so that the distal end is inserted within the interior of the bone. The upper surface of the blade may include at least one channel. The blade may include a bore extending from its proximal end to its distal end, the bore being dimensioned and configured to receive a guide wire. The first included angle between the lower surface of the first portion and the lower surface of the second portion ranges from about 75° to about 150° and, more preferably about 75° to 110° or about 145° to about 120° depending upon the plates application.

The second central axis of the second hole portion of the bone plate may be angled so as to substantially intersect the second longitudinal axis at a point below the lower surface of the first portion of the bone plate. The first longitudinal axis of the bone plate may define a plane that bisects the first portion of the bone plate and the second central axis may intersect the plane at a single point. The second central axis may be angled with respect to the first central axis and the angle may range from about 10° to about 35°. The second hole portion of the bone plate may be configured to receive the bone anchor in a manner so that the shaft is substantially at a fixed angle with respect to the second portion of the bone plate. At least a portion of the second hole portion may be threaded for threadably engaging a threaded head of a bone anchor, the second hole being configured to fix the bone anchor at an angle relative to the second portion of the bone plate. The threaded portion of the second hole portion may extend along the periphery relative to the second central axis at an angle from about 190° to about 280°.

A bone anchor having a threaded head may be supplied which threadably engages with the threaded portion of the second hole portion. The bone anchor may be configured and dimensioned so as to contact at least a portion of the second portion of the bone plate. The first hole portion of the bone plate may be smooth and may be elongated in the direction of the first longitudinal axis. At least a portion of the second hole portion may conically taper from the upper surface to the lower surface. The first hole portion may be elongated in the direction of the first longitudinal axis and may include a first substantially spherical counterbore along the upper surface and a second counterbore along the lower surface of the bone plate. A bone anchor having a spherical head may be supplied and the first counterbore may be configured to engage the spherical head for compression or distraction of the fracture.

The bone plate according to another embodiment may include an elongated plate portion having a first longitudinal axis, an upper surface and a lower surface and a blade portion having a second longitudinal axis, an upper surface and a lower surface, the blade portion being angled with respect to the plate portion. The plate portion may have at least one hole for receiving a bone anchor having a shaft, the hole having a first portion defining a first central axis substantially perpendicular to the lower surface and the hole may include a second portion overlapping and in communication with the first portion and having a second central axis substantially angled with respect to the blade portion. At least a portion of the periphery of the second hole portion may be threaded, the second hole portion being configured to threadably receive the bone anchor such that the shaft is substantially coaxially aligned with the second central axis and threadably and angularly fixed with respect to the blade portion. The portion of the periphery of the second hole portion that is threaded angularly ranges about the second central axis from about 190° to about 280°. The bone anchor may be a bone screw having a threaded shaft and a threaded head. The bone screw may be received in the second portion of the hole so that the threaded shaft is angled with respect to the blade portion so as to form a truss. Preferably the threaded head is engaged with the threaded portion of the periphery of the second portion of the hole so as to lock the bone plate with respect to the bone screw. At least a portion of the second hole portion may conically taper from the upper surface to the lower surface.

The first hole portion may be elongated in the direction of the first longitudinal axis and may include a first substantially spherical counterbore along the upper surface and a second counterbore along the lower surface of the bone plate. The first counterbore may be configured to engage the spherical head for compression or distraction of the fracture. The hole may be located on bone plate such that at least one of the first and second central axes is spaced a distance from the first longitudinal axis of the elongated plate portion.

The bone plate according to another embodiment may comprise an elongated plate portion having a first longitudinal axis, an upper surface and a lower surface and a blade portion having a second longitudinal axis, an upper surface and a lower surface, the blade portion being angled with respect to the plate portion and further being configured to be inserted into the interior of the bone. The plate portion may have at least one threaded hole having a central axis, the hole being configured for threadably receiving a bone anchor having a shaft such that the shaft is substantially aligned along the central axis and the hole is angled relative to the blade portion such that the central axis intersects the second longitudinal axis at a point below the lower surface of the bone plate to form a truss. The threaded hole may conically taper from upper to lower surface. The bone anchor may be a bone screw having a threaded head and a threaded shaft, the bone screw received in the at least one threaded hole such that the threaded head of the bone screw is threadedly engaged with the at least one hole so as to fix the bone plate relative to the bone screw. The bone screw may be a suitable length so that at least a portion of the shaft contacts the blade portion of the bone plate.

The bone plate may comprise at least a second threaded hole spaced relative to the first threaded hole, the second hole having a central axis, the hole being configured for threadedly receiving a bone anchor having a shaft such that the shaft is substantially aligned along the central axis of the second hole, and the second hole may be angled relative to the blade portion such that central axis of the second hole intersects the second longitudinal axis at a point below the lower surface of the bone plate to form a truss. The central axis of the second threaded hole may be angled relative to the central axis of the at least one other threaded hole such that a bone anchor received in the second threaded hole is operatively associated with a bone anchor received in the at least one other threaded hole.

According to another embodiment a bone plate system may be provided which comprises at least one bone anchor having a shaft and a head portion, a bone plate having an elongated plate portion having a first longitudinal axis, an upper surface and a lower surface and a blade portion having a second longitudinal axis, an upper surface and a lower surface, the blade portion being angled with respect to the plate portion so as to define an included angle therebetween ranging between about 75° and about 150°, and, more preferably about 81° to about 95°, the plate portion having at least one hole, the hole having a first portion defining a first central axis and including a first counterbore along the upper surface, the first hole portion being configured to receive the bone anchor such that the head is in sliding engagement with the first counterbore; and the hole includes a second hole portion in communication with the first hole portion from the upper surface to the lower surface and defining a second central axis angled with respect to the blade portion, the second hole portion including a second counterbore, the second hole portion being configured to receive the bone anchor such that the shaft is substantially coaxially aligned with the second central axis and the head portion is fixedly engaged with second counterbore.

The second counterbore may be threaded and the head portion of at least one bone anchor may be threaded, the second counterbore being configured for fixed threaded engagement with the head portion of the bone anchor. Alternatively, the second counterbore may be smooth and the head portion of the at least one bone anchor may be threaded. Alternatively still, the second counterbore may be threaded and the head portion of the bore anchor may be smooth. Still further, the second counterbore may be smooth and the head portion of the bone anchor may be smooth. The first and second central axes may be spaced a distance from the first longitudinal axis. The upper surface of the blade may include at least one channel, and the blade may include a bore extending from proximal to distal end, the bore being dimensioned and configured to receive a guide wire.

BRIEF DESCRIPTION OF THE DRAWINGS

The detailed description will be better understood in conjunction with the accompanying drawings, wherein like reference characters represent like elements. It should be understood that the features described in the illustrated drawings may exist singularly or in combination and that the invention is not limited to the embodiment disclosed in the figures which are illustrative only and for the purposes of description and not limitation.

DETAILED DESCRIPTION OF THE PREFERRED EMBODIMENTS

Figure 1:
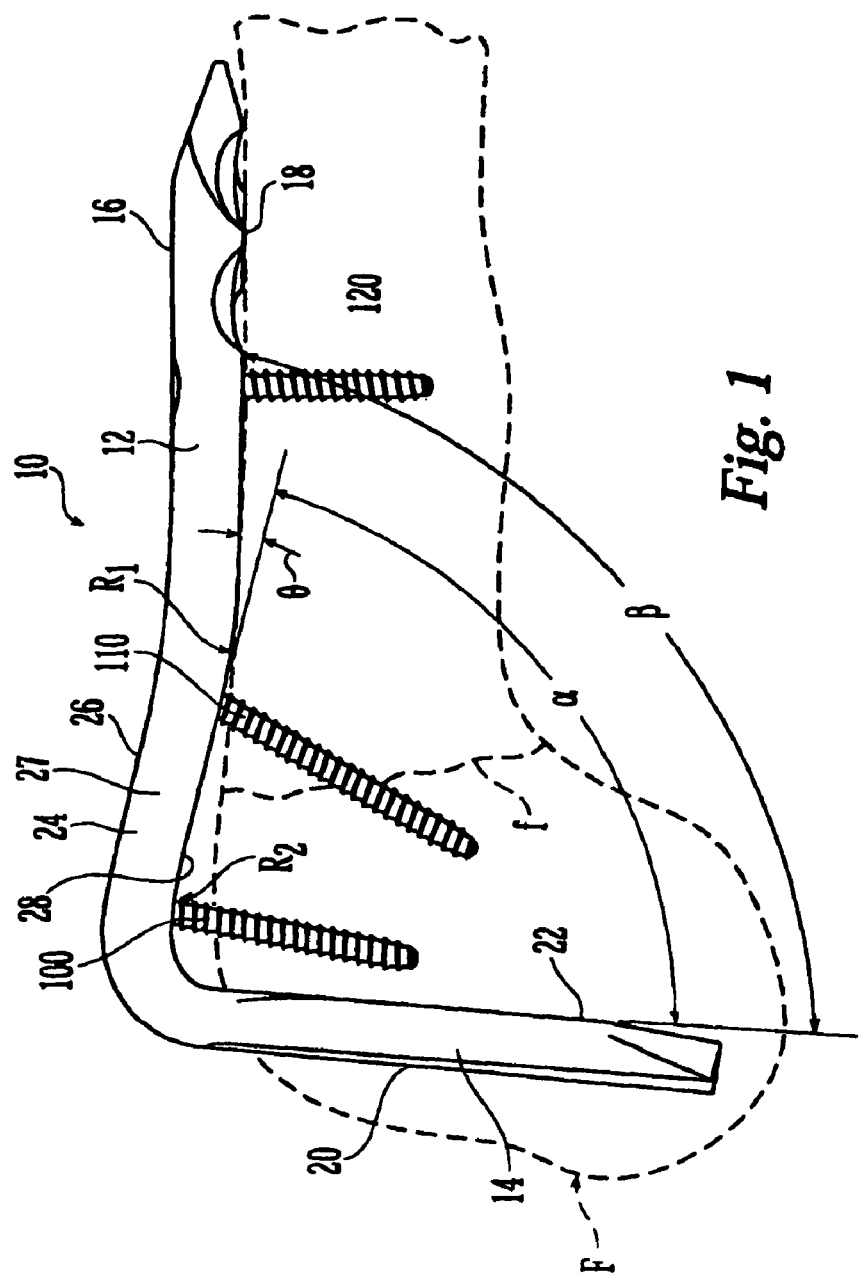
FIG. 1 is an illustrative embodiment of a bone plate attached to a bone F having a fracture f.

Shown in FIG. 1 is a first illustrative embodiment of bone plate 10 for use in internal fixation, compression and/or distraction of a bone, for example, the proximal portion of femur F, having a fracture f. One of ordinary skill in the art will know and appreciate, however, that the principles of the present invention may be applied to bone plates for fixation of other bones of humans and/or animals, such as, for example, long bones including the tibia, humerous, fibula, radius, ulna and for different parts or portions of long bones (e.g., the distal femur).

Bone plate 10 includes a first portion 12 that is configured to lie substantially parallel to the surface of bone F anchored by a plurality of bone anchors 100, 110, 120. Preferably, first portion 12 is substantially elongated and, preferably, substantially straight, as illustrated in FIG. 1. The elongated plate portion 12 includes an upper surface 16 and a lower or bone surface 18. The bottom or lower surface 18 may be curved to better conform to the bone to which it is intended to attach. Likewise, the upper surface 16 may also be curved or contoured. The width of the first portion 12 may be substantially uniform and may range from approximately 8 millimeters (mm) to approximately 24 mm and is more preferably about 12 mm to about 20 mm. The bone plate 10 illustrated in FIG. 1 has a width of approximately 16 mm. The thickness of the plate may generally range from about 4 mm to about 12 mm, and, more preferably, about 6 mm to about 9 mm. The bone plate illustrated in FIG. 1 has a thickness of approximately 7 mm to about 8 mm. The length of bone plate may vary, with exemplary lengths ranging from about 60 mm to about 150 mm, and more preferably about 80 mm to about 120 mm. The bone plate of FIG. 1 has a length of about 100 mm to about 105 mm. One of skill in the art will appreciate that the width, thickness and may vary beyond the exemplary ranges provided and will depend upon the application of the bone plate and the intended patient. The first portion 12 may be anchored such that the lower surface 18 of first portion 12 contacts the bone F directly, or alternatively, the first portion 12 may be held at a distance from the bone surface. Keeping bone plate 10 from contacting the bone may facilitate increased blood flow over the fracture zone.

Bone plate 10 further includes a second portion 14 configured to be inserted and anchored into bone tissue, for example, the condyle of bone F as shown in FIG. 1. Preferably, the second portion 14 forms a blade insertable in the condyle to lag or attach the bone plate 10 to the bone F. The second portion 14 also includes an upper surface 20 and lower surface 22. Preferably, bone plate 10 is made from a single piece of material such that first portion 12 and second portion 14 are integral with one another; alternatively, first portion 12 and second portion 14 may be joined together by means known to those of ordinary skill in the art. Moreover, second portion 14 is oriented with respect to first portion 12 such that the lower surface 22 and lower surface 18 form an included angle β. Preferably, angle β ranges from about 75° to about 150° and more preferably may range from about 145° to about 120°, or from about 75° to about 110° depending upon its application. In FIG. 1 the angle is between 81° and about 95° for bone plate 10 in which blade portion 14 is inserted into the condyle.

Bone plate 10 may optionally include a third portion 24 having upper surface 26 and a lower surface 28. Third portion 24 may be bent or angled with respect to the second portion 14 such that the lower surface 28 and lower surface 22 of blade portion 14 form an included angle α, wherein α ranges from approximately 75° to approximately 85° and preferably is about 81°. Angle α is different than and preferably less than angle β. The degree of bending between the first portion 12 and third portion 24 will vary depending upon the application of the plate but may vary between an angle θ of about 0° and about 25° and, more preferably, may vary from about 14° to about 16°. Alternatively, third and first portions 12, 24 may be configured and integrated such that their lower surfaces 18, 28 define a single lower surface at a single relative angle β with respect to lower surface 22 of second portion 14. Third portion 24 is preferably integrated with first portion 12 and second portion 14. Third portion 24 is attached by a plurality of bone anchors 100, 110. Preferably, third portion 24 is substantially elongated and may be configured such that the third portion 24 may be anchored such that the lower surface 28 contacts bone F directly, or alternatively third portion 24 may be held at a distance from the bone surface.

The third portion 24 can be substantially arcuate having a constant radius of curvature or a radius of curvature that varies over its length. Alternatively or additionally, the third portion 24 may include one or more relatively straight sections. The relatively straight sections may be connected by other segments having a radius of curvature. In the embodiment shown in FIG. 1, the third portion 24 has a straight section 27 connected to the first portion 12 with a radius of curvature R1 of about 95 mm and connected to the second portion 14 with a radius of curvature R2 of about 90 mm. The radius of curvature R1 and R2 may vary from exemplary values from about 30 mm to about 150 mm depending upon the application of the bone plate. One of skill in the art will appreciate that the radius of curvature R1, R2 can also vary outside the exemplary range.

Figure 2:
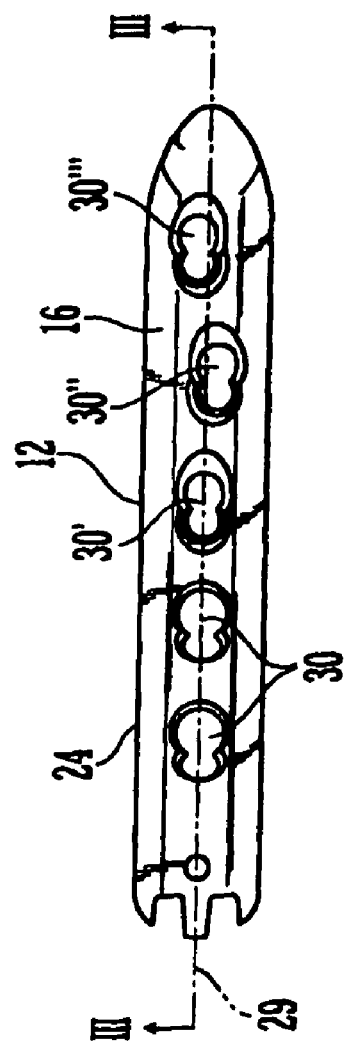
FIG. 2 is a top view of a portion of the bone plate of FIG. 1.
Figure 15:
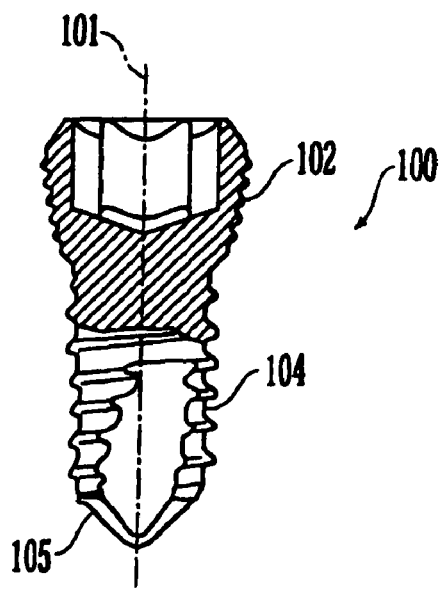
FIG. 15 is an illustrative embodiment of a bone anchor.
Figure 16:
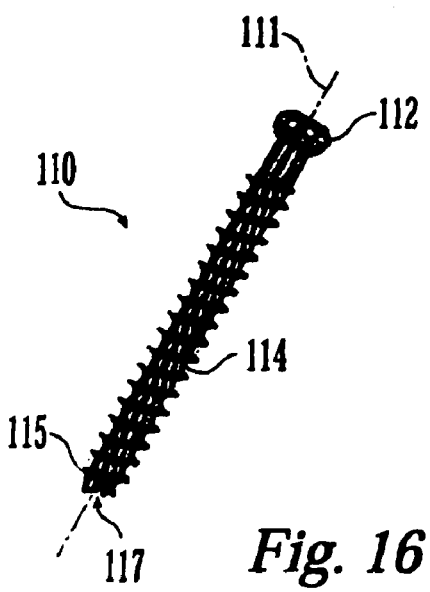
FIG. 16 is another illustrative embodiment of a bone anchor.

FIG. 2 shows a plan view of upper surface 16 of integrated first elongated plate portion 12 and optional third portion 24. Elongated plate portion 12 and optional portion 24 define a longitudinal axis 29 and includes a plurality of bone plate holes 30 for receiving a bone anchor, for example bone screw 100, to anchor bone plate 10 to the surface of bone F. Although it is contemplated that the bone anchor 100, 110, 120 may be in the form of a bone screw having a head and a threaded shank (for example any one of the types shown in FIGS. 15–16), other bone anchors known to one of ordinary skill in the art, such as blades, nails, pins, etc., may be used. Referring to FIGS. 15 and 16, bone screw 100 has a central axis 101, a shaft in the form of a threaded shank 104, a tip 105, and a threaded head 102, while bone screw 110 similarly has a central axis 111, a threaded shank 114, and a tip 115, however, bone screw 110 has a partially spherical head 112 without threads. Other geometries and configurations are possible for the bone screw. Either of bone screws 100, 110, 120 may be constructed from, for example, titanium, alloys of titanium, stainless steel, resorbable materials such as polymers, allograft or other biocompatible materials known in the art. Bone screws 100, 110, 120 are preferably compatible with the bone plate 10 in terms of composition and strength. Bone screws 100, 110, 120 may be cannulated, as shown in FIG. 16 with a through bore or channel 117 extending from the head 112 to the tip 115, for introducing instruments, for example, a guide wire.

Shown in FIG. 2, elongated plate portion 12 may include second, third, fourth and fifth holes or as many holes 30, 30', 30", etc. as is necessary, but usually at least two holes 30, to effectively anchor bone plate 10 or perform compression and distraction of bone F about the fracture site or both. The holes of elongated plate portion 12, and optional third portion 24 may take many different forms, and may be substantially aligned along longitudinal central axis 29 or alternatively, any one of holes 30 may be offset laterally to either side of or aligned with longitudinal central axis 29.

Figure 3:
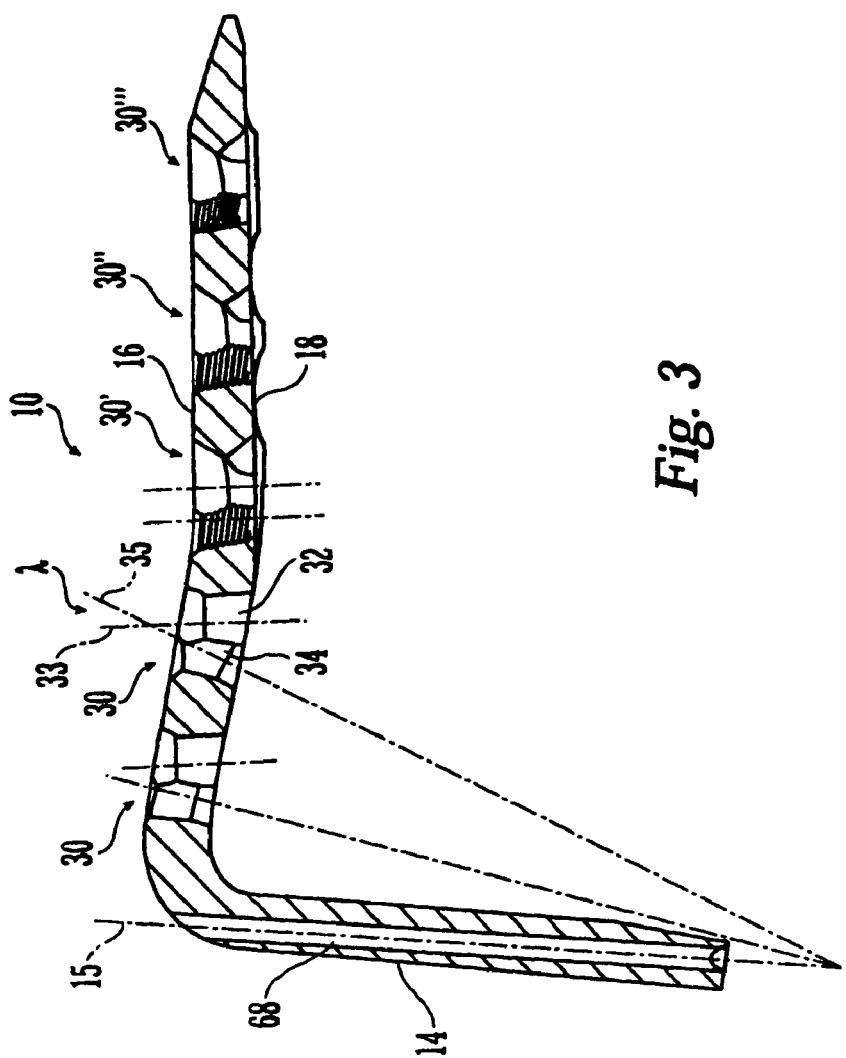
FIG. 3 is a cross-sectional view of the bone plate of FIG. 1 taken along the line III—III in FIG. 2.

FIG. 3 illustrates a preferred embodiment of bone plate 10 which includes a plurality of holes 30 located in optional third portion 24, in this case two holes 30, and a plurality of bone plate holes 30', 30", 30"' in this case three holes 30', 30", 30"' located in first portion 12. Although bone plate holes 30', 30", 30"' may be different, in FIG. 3 they are substantially the same and will be described with reference to bone plate hole 30' for ease of reference. Bone plate hole 30' may be substantially the same as bone plate holes 30 or preferably may be configured to be substantially the same as bone plate holes 330 described in reference to FIGS. 9–12. Bone plate holes 30 are preferably aligned along the longitudinal central axis 29 as illustrated in FIG. 2, however, bone plate holes 30 may be offset from longitudinal central axis 29. Bone plate holes 30 may be offset on the same side of the central axis 29, on different sides, or one or more bone plate holes 30 may be aligned with the longitudinal central axis 29 while one or more bone plate holes are offset from central axis 29.

One or more bone plate holes 30' in the first portion 12 may be aligned with the central axis 29 or laterally offset on the same side or different sides of the central axis 29. The bone plate holes 30' may be offset on either side or the same side as the central axis 29. Thus, the bone plate holes 30' may be arranged in any combination of aligned or offset configurations. In the preferred configuration shown in FIG. 2, the bone plate holes 30' may have the central axis of one hole 30' aligned with the central axis 29 and the central axis of the other two holes 30' offset on a different side of the axis. The central axis of the holes 30' may be offset any distance from the central axis but are preferably offset from about 0 to about 4 mm from the central axis and more preferably about 1 mm to about 2 mm. The holes 30' in bone plate 10 shown in FIG. 3 are offset approximately 1.6 mm.

Figure 5:
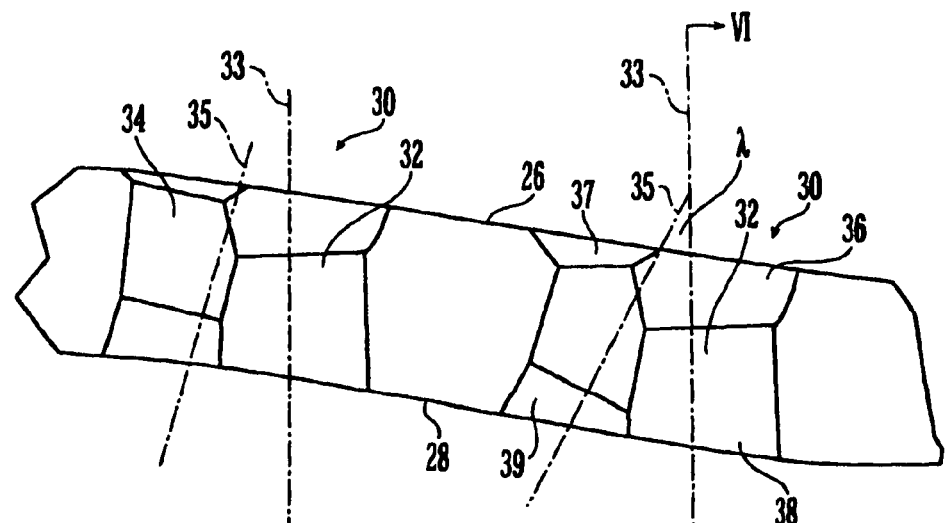
FIG. 5 is a cross-sectional view of another illustrative embodiment of bone plate holes.
Figure 4:
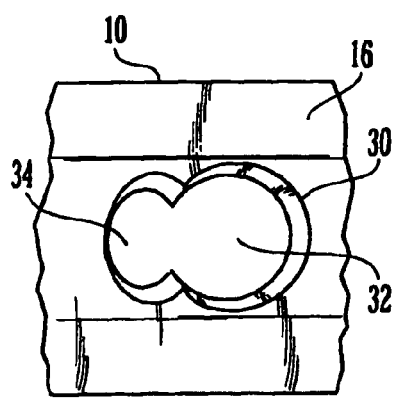
FIG. 4 is an illustrative embodiment of a bone plate hole.

Shown in FIGS. 4 and 5 is a first illustrative embodiment of bone plate hole 30 having a first hole portion 32 and second hole portion 34 overlapping and in communication with the first hole portion 32. First hole portion 32 defines a central axis 33 and may have a first counterbore 36 along the upper surface 26 and second counterbore 38 along the lower surface 28. Preferably, the first counterbore 36 and the second counterbore 38 are substantially smooth. The second hole portion 34 may also define a second central axis 35 and include first counterbore 37 and second counterbore 39 along upper and lower surfaces 26, 28 respectively. As seen in FIG. 3, second central axis 35 may be angled with respect to first central axis 33 at an angle λ, which may preferably range from about 10° to about 35°, and, more preferably, from about 16° to about 28°.

Figure 6:
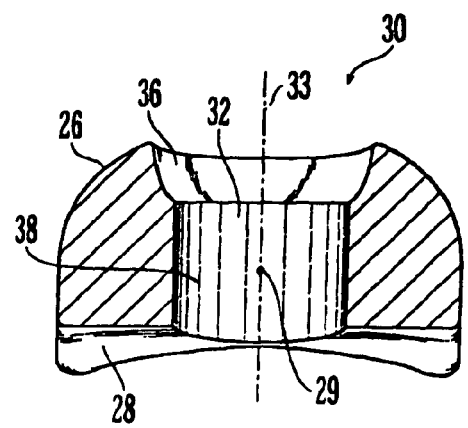
FIG. 6 is cross-sectional view of the bone plate hole in FIG. 5 taken along the line VI—VI.

First central axis 33 of first hole portion 32 may be oriented substantially perpendicular to at least a portion of the lower surface 18 which may lie substantially parallel to the surface of bone F. First counterbore 36 may be configured to engage the head of a bone anchor 110. Counterbore 36 may be configured so as to align the shank of bone screw 110 substantially along the first central axis 33. Preferably, counterbore 36 is substantially smooth and also partially spherical, as is shown in FIG. 5 and FIG. 6, and a bone screw 110 having a spherical head 112 may be inserted and oriented at a surgeon selected angle with respect to first counterbore 36 so as to apply compressive or distraction forces about the fracture f upon engagement of the spherical head 112 with the first counterbore 36.

Referring again to FIG. 3, the second hole portion 34 may be configured and the second central axis 35 may be angled so that upon receiving a bone anchor, for example, bone anchor 110 of the type shown in FIG. 15, the shank 114 of bone anchor 110 is substantially aligned along the second central axis 35 in an angled relationship with respect to blade portion 14 having longitudinal axis 15. More specifically, second hole portion 34 may be configured such that the second central axis 35 and the longitudinal axis 15 of blade portion 14 intersect at a point below the lower surface 18 to define a plane. Preferably the second counterbore 39 is conically tapered so that its width decreases from the first counterbore 37 to the lower surface 28. In addition, the second counterbore 39 is preferably threaded or at least partially threaded. The thread may partially or fully extend from upper surface 26 to lower surface 28. Preferably the thread extends along the periphery of the second counterbore from about 190° to about 280°. In this manner, a screw such as screw 200 shown in FIG. 15 inserted into the second portion 34 of bone plate hole 30 will be threaded into the bone plate 10 and fixed into an angular position such that it is locked with the bone plate so that axis 101 will substantially coincide with axis 35 of the second hole portion 34. Bone plate hole 30 may be the same as or similar to the bone plate hole described in U.S. Pat. No. 6,669,701 which disclosure and description is incorporated herein by reference.

Figure 17:
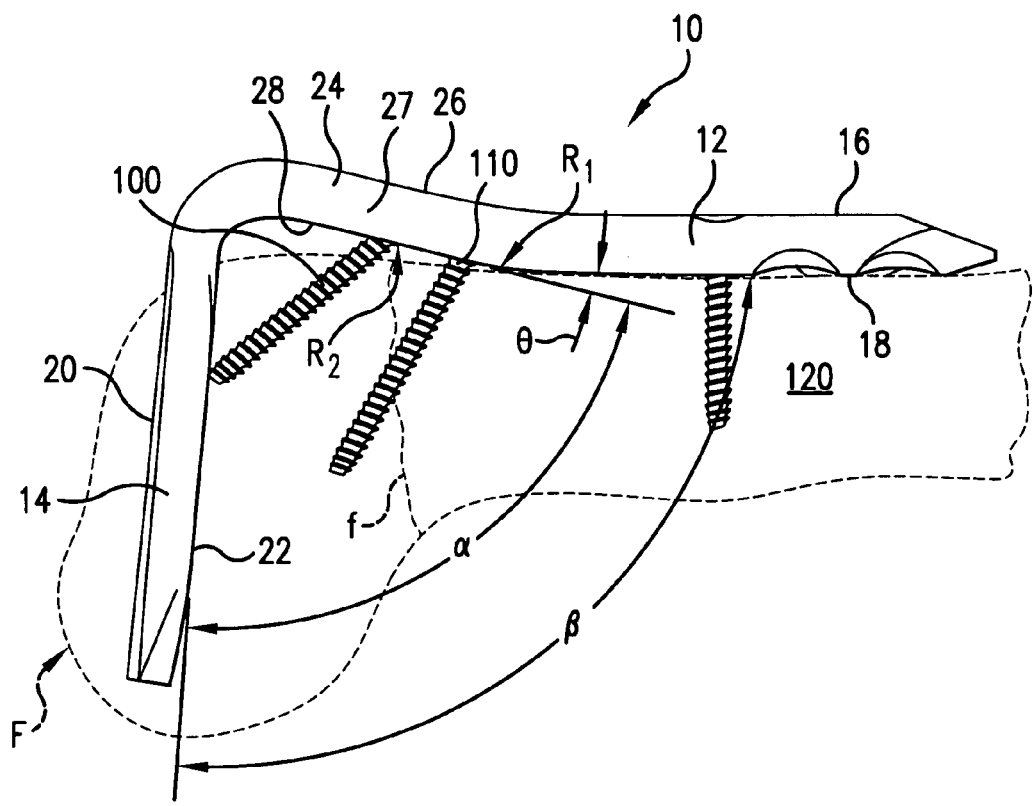
FIG. 17 is a side elevation view of yet another bone plate according to a preferred embodiment of the invention, showing at least one bone anchor contacting a blade portion of the bone plate.

Referring again to FIG. 1, in a preferred embodiment, at least one of the bone plate holes 30, is provided in the plate portion 24 and is configured so as to receive a bone anchor such that the shaft of the shank is directed towards and angled with respect to the blade portion 14 thereby forming a truss or substantially rigid construct to improve anchorage of bone plate 10 in bone F. The truss improves the anchorage by distributing loads and stresses experienced at the interface of the anchor and perimeter of the hole in the base plate. In addition, the bone anchor 100, 110 may be selected of such a length so as to contact or nearly contact the lower surface 22 of blade portion 14, as shown in FIG. 17. Where bone anchor 110 is of sufficient length, bone anchor 110 received in the second hole portion 54 may contact or nearly contact blade portion 14 anywhere along the length of the lower surface 22. The bone plate 10 may be provided with any number of bone plate holes each configured to receive and direct a bone anchor in any manner relative to the blade portion 14 or one another so as to produce a rigid stable construct for fixation, compression or distraction of bone F. Orientation of any bone anchor 100, 110, 120 engaged with bone plate 10, relative to the first, second and third bone plate portions 12, 14, 24 is facilitated by the configuration of bone plate hole 30, 30', and the bone plate holes 230, 230', 230", 330 which are described in greater detail below.

As additional bone holes 30 are added as needed to elongated plate portion 12, the second hole portion 34 of each additional hole 30 may be variably configured so as to angle the second central axes 35 of each hole 30 relative to the blade portion 14 in a manner that produces the desired stable fixation. Preferably, the second central axis 35 of each hole 30 will be configured to intersect the longitudinal axis 15 of blade portion 14 at a point below lower surface 18. Each additional bone anchor received in each additional second hole portion 34 and aligned with second central axis 35 may form a truss with and support blade portion 14. Each additional bone anchor may contact or nearly contact blade portion 14 or other bone anchor at a point below the lower surface 18, 28. The bone anchors may contact or nearly contact blade portion 14 anywhere along its length or the length of a different bone anchor.

As seen in FIG. 6, second counterbore 38 of first hole portion 32 may be substantially cylindrical having a constant diameter from lower surface 28 until first counterbore 36. Alternatively, either first or second hole portions 32, 34 may include a portion that conically tapers so that the diameter of the partial hole decreases in the direction toward lower surface 28. In addition, either first hole portion 32 or second hole portion 34 or both may have a portion of their periphery threaded for engagement with a threaded shank or the threaded head of a bone anchor, for example, the bone anchor 100 shown in FIG. 15, in order to threadedly lock the bone anchor 100 in a fixed angular relationship relative to the first bone plate portion 12 and third bone plate portion 24. The thread or threads may partially or fully extend from upper to lower surface 26, 28. Either first or second portions 32, 34 alternatively may include smooth portions. When the central axis 33 of first hole portion 32 intersects the longitudinal central axis 29 of bone plate 10, a plane may be defined common to both axes 29, 33 which bisects bone plate 10. Preferably first hole portion 32 is substantially smooth and elongated while second hole portion is circular and threaded at least partially around its periphery. Preferably second hole portion 34 is threaded from about 190° to about 280°. Any bone plate hole 30, 30' of bone plate 10 may be configured in a manner substantially similar to the bone plate holes disclosed in U.S. Pat. No. 6,669,701 which is incorporated herein by reference thereto.

Figure 7:
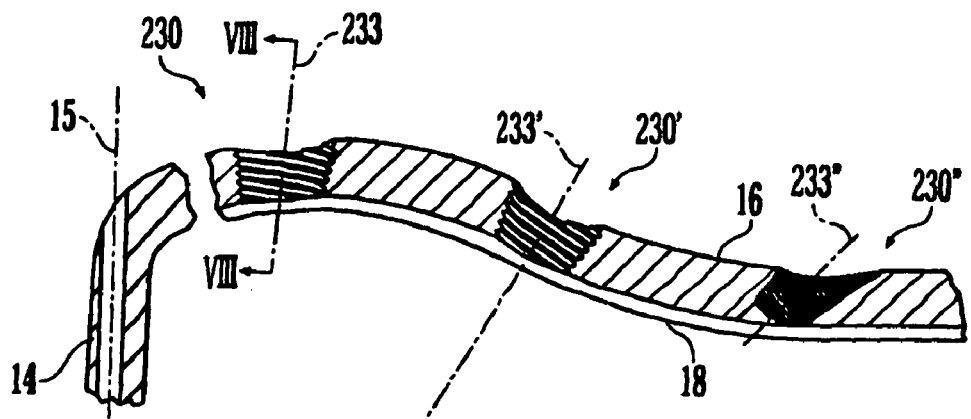
FIG. 7 is another cross-sectional view of another illustrative embodiment of bone plate holes.
Figure 8:
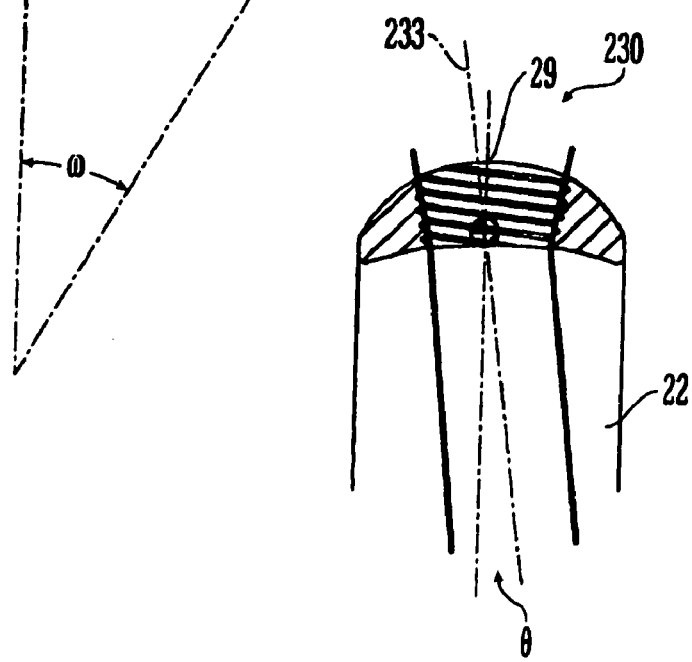
FIG. 8 is cross-sectional view of the bone plate hole in FIG. 7 taken along the line VIII—VIII.

Shown in FIGS. 7 and 8 is an illustrative embodiment of bone plate hole 230. Hole 230 may be located in first portion 12 but preferably in third portion 24 of the bone plate 10 and may contain a central axis 233 along which the shaft of a bone anchor would be substantially aligned and extend. Moreover, bone plate hole 230 may be configured such that the central axis 233 may intersect the longitudinal axis 15 of blade portion 14 at a point below the lower surface 18, lower surface 28 or both. Once again, a bone anchor having a shank substantially aligned with the central axis 233 may form a truss with blade portion 14 for improved anchorage of bone plate 10. The axis 233, 233', 233" may form an angle w with the axis 15 of the blade portion 14. The angle w may vary from about 0° to about 45° degrees. The angle w in the bone plate shown in FIG. 7 between axis 15 and axis 233 is about 5°, between axis 15 and axis 233' is about 30°, and between axis 15 and axis 233" is about 45°.

Hole 230 may be configured for engaging the head of a bone anchor. More preferably, hole 230 may be configured for fixing and locking the bone anchor in a fixed and predetermined orientation with respect to the blade portion 14 or the exterior surface of the bone F into which the anchor is inserted, for example, by threaded, interference or press fitted engagement, or any other form of engaging the head of bone anchor with plate hole 230 along a predetermined and fixed axis as would be known to one of ordinary skill in the art. In the illustrative embodiment shown in FIG. 7, hole 230 is threaded for respective engagement, with bone anchors, for example bone anchor 100 of FIG. 15 having threaded head 102. As seen in FIG. 7, threaded hole 230 may be conically tapered so that its diameter decreases in a direction toward the lower surface 18 of bone plate 10. The tapering of hole 230 may facilitate alignment between the threads of hole 230 and the threads on the head 102 of bone screw 100. Alternatively, threaded hole 230 may be substantially cylindrical, partially spherical or other shapes known in the art. As is more clearly shown in FIG. 8, the central axis 233 of hole 230 may define an angle θ relative to a plane that includes longitudinal axis 29 and substantially bisects the bone plate 10. The angle θ may vary from about 0° to about 10° although other variations and angles are possible.

The threaded engagement of the bone plate hole 230 and the threaded head 102 prevents movement of bone plate 10 with respect to bone screw 100 and locks the angular position of the threaded shank 104 relative to the blade portion 14. With the threaded shank 104 of a bone screw 100 anchored to the fractured bone f and the threaded head 102 lockingly engaged with the threaded hole 230, bone plate 10 is fixed to the bone F, and depending on the depth with which the threaded shank 104 is inserted into the bone, the lower surface 18 of the bone plate 10 may directly contact the bone surface, similar to the configuration shown in FIG. 1, or alternatively, bone plate 10 may be affixed and spaced at a distance from the bone surface. In addition, when the shank 104 is of sufficient length so as to span across the fracture zone f, the hole 230 may be configured so as to align the shank 104 at such an angle with respect to the elongated plate portion 12 so as to reduce the gap of the fracture f upon locking of the threaded head 106 in the threaded hole 230.

As previously explained, bone plate 10 may be provided with as many bone plate holes as are required for the surgical procedure. Accordingly, bone plate 10 may be provided with a plurality of bone plate holes configured as hole 230. Each hole may be configured as described above but vary by the angle of orientation w relative to the blade portion 14. For example, as is shown in FIG. 7, bone plate 10 includes first hole 230 having central axis 233, and bone plate 10 additionally includes second and third holes 230', 230" having central axes 233' and 233" respectively. First, second and third holes 230, 230', and 230" are spaced relative to one another in the direction of elongation of plate 10, and each is threaded and conically tapered in the direction from upper surface 16 to lower surface 18. The angle of their respective central axes 233, 233' and 233" of the three holes 230, 230' and 230" relative to the blade portion 14 may vary for each axes. Thus, each bone anchor received and threadably located in holes 230, 230', and 230" is threadedly aligned with central axes 233, 233' and 233" and may form a truss with blade portion 14 as previously described with respect to bone hole 30. In addition, any one of holes 230, 230' and 230" may be configured such that its central axis intersects the central axis of another bone plate hole provided on plate 10 operatively associating the two bone anchors received therein. For example, an anchor received in hole 230, 230' and 230" configured as described above may contact or nearly contact another bone anchor received in a bone plate hole 30 or 30' located on bone plate 10. The bone anchors may contact or nearly contact at the tip or any other point along the shanks of the bone anchors.

Figure 9:
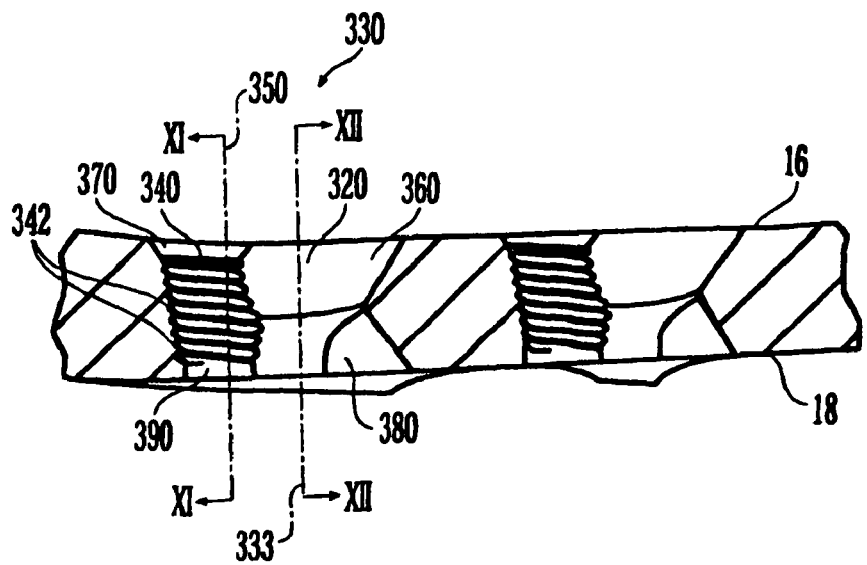
FIG. 9 is another cross-sectional view of another illustrative embodiment of bone plate holes.
Figure 10:
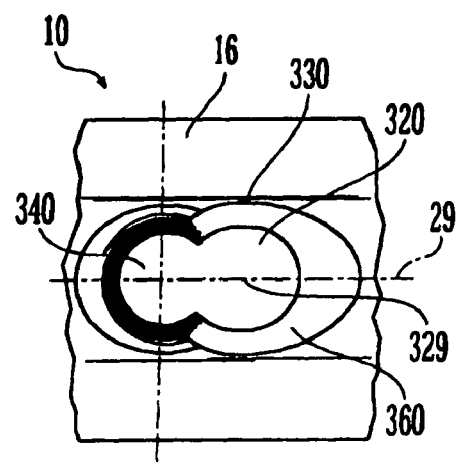
FIG. 10 is a top-view of the bone plate hole of FIG. 9.
Figure 12:
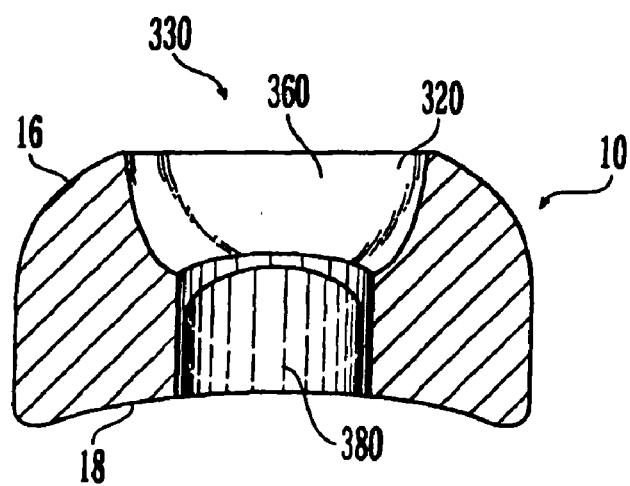
FIG. 12 is a cross-sectional view of the bone plate hole of FIG. 9 taken along the line XII—XII.

Bone plate 10 may preferably be alternatively configured with one or more combination holes 330 shown in FIGS. 9 and 10. Combination hole 330 may contain a first hole portion 320 and a second hole portion 340, in which the second hole portion 340 overlaps and is in communication with the first hole portion 320. The second hole portion may overlap and be in communication with the first hole portion 32 from upper surface 16 to lower surface 18. First hole portion 320 may preferably be elongated in the direction of the longitudinal axis 29 of bone plate 10. Alternatively the first hole portion may be elongated in a direction that is transverse to the longitudinal axis 29 of the bone plate 10. While the axis 329 of the elongated first hole portion 320 is shown in FIG. 10 as aligned and coincident with axis 29 of the bone hole it will be appreciated that the axis 329 of the elongated first hole portion may be laterally offset to either side of the bone plate axis 29 as illustrated by holes 30' and 30''' in FIG. 2. First hole portion 320 may define a first central axis 333 and preferably includes a first counterbore 360 along the upper surface 16 and a second counterbore 380 along the lower surface 18. As seen in FIG. 12, first counterbore 360 may preferably be substantially smooth and spherical for engagement with a bone anchor having a spherical head, for example, head 112 of bone screw 110 in FIG. 16. Bone screw 110 may be received in first hole portion 320 such that the spherical head 112 engages first counterbore 360 so as to bias the bone plate 10 to provide compression or distraction of the bone fracture f. Second counterbore 380 may be similarly preferably spherical to facilitate angled reception of bone anchor 110 in first hole portion 320 or second counterbore 380 may be substantially partially cylindrical.

Figure 11:
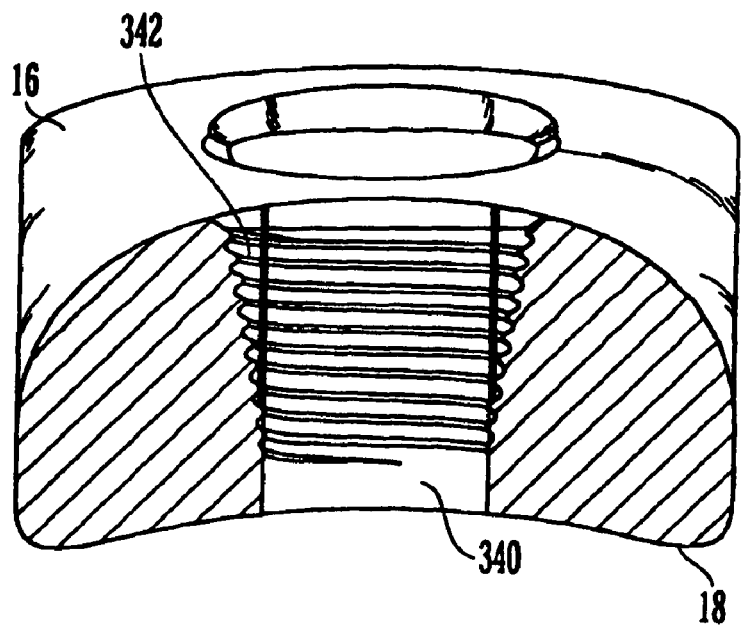
FIG. 11 is a cross-sectional view of the bone plate hole of FIG. 9 taken along the line XI—XI.

Referring again to FIGS. 9 and 10, second hole portion 340 may preferably be substantially circular defining a second central axis 350 which may preferably be substantially parallel to axis 333. Second hole portion may similarly include a first counterbore 370 along the upper surface 16 and a second counterbore 390 along the lower surface 18. Second hole portion 340 may preferably define along a portion of its periphery a screw thread 342 for threadedly locking a bone anchor in a fixed angled relationship relative to the elongated plate portion 12. The thread 342 may extend along the periphery relative to central axis 350 at an angle from about 190° to about 280°. Screw thread 342 may preferably be engaged by the threaded head portion 102 of bone screw 100, for example, shown in FIG. 15. Screw thread 342 may be disposed in a single plane or in several planes. The planes(s) may be parallel to upper surface 16 and/or to lower surface 18. Alternatively, the planes may be angled relative to the upper surface 16 or the lower surface 18 in order to angle a bone anchor relative to the at least a portion of the bone plate 10. As seen in FIG. 11, thread 342 may preferably substantially extend from upper surface 16 to lower surface 18 of bone plate 10, and second hole portion 340 may preferably conically taper from upper surface 16 to lower surface 18. Referring back to FIG. 3, bone plate 10 is shown having at least three holes configured substantially similarly to hole 330. In addition, second hole portion 340 may be angled relative to upper surface 16 and/or lower surface 18, such that a bone anchor, for example bone screw 100, received in second hole portion 340 is acutely angled relative to at least a portion of bone plate 10. For example, bone hole 230 may be located on bone plate 10 with second central axis 350 intersecting longitudinal axis 15 of blade portion 14 at a point below the lower surface 18, such that bone anchor 100 is threadably received in second hole portion 340 in a fixed and locked relationship relative to blade portion 14. As a result, shank 104 of bone screw 100 may be directed toward blade portion 14 of plate 10 so as to form a truss in a manner substantially similar to the truss described above.

Bone plate holes configured as holes 30, 30', 230, 330 may be located anywhere along elongated plate portion 12 of bone plate 10 such that the central axes 333 and 350 intersect and align with the longitudinal axis 29 of bone plate 10, or alternatively, the holes 30, 30', 230, 330 may be located along elongated plate portion 12 such that either central axis 333 or 350 is spaced relative to the longitudinal axis 29 of bone plate 10.

Figures 13, 14:
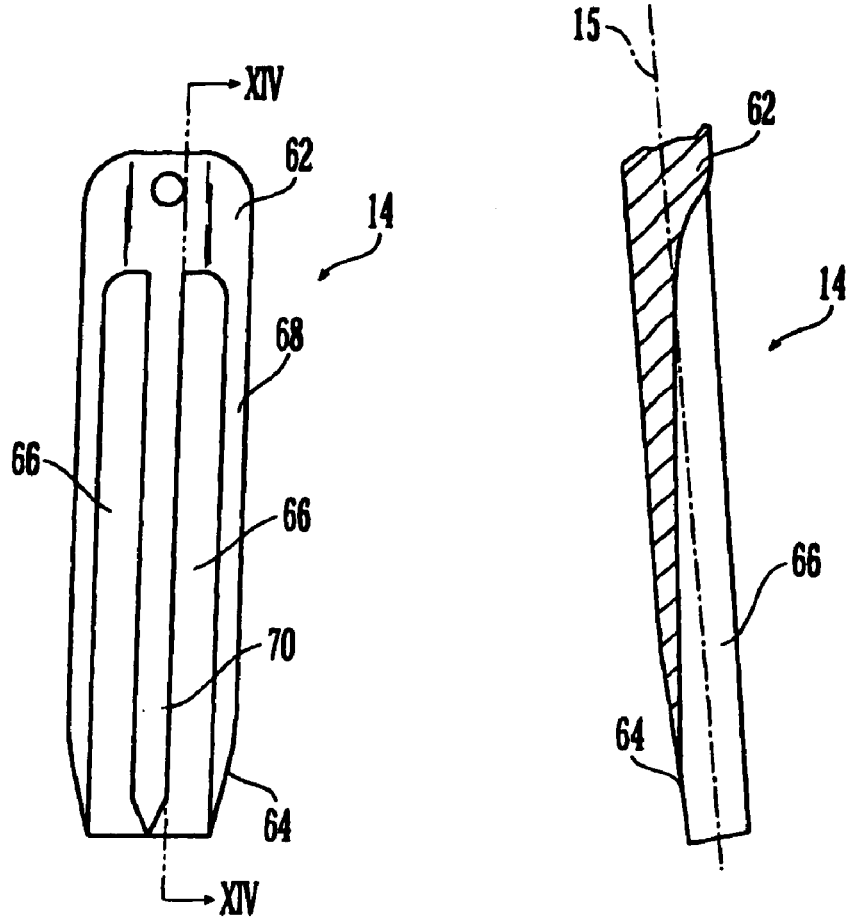
FIG. 13 is a plan view of an illustrative embodiment of a portion of the bone plate of FIG. 1.
FIG. 14 is a cross-sectional view of the portion of the bone plate of FIG. 14 taken along the line XIV—XIV.

Referring now to FIGS. 13 and 14, blade portion 14 of bone plate 10 is shown having a longitudinal axis 15, a proximal end 62 adjacent elongated plate portion 12, and a distal portion 64. The width at the distal end 64 preferably tapers in the direction toward the distal end 64. The upper surface 20 may include at least one channel 66 running longitudinally defined by at least one side wall 69, the channels thereby minimizing the amount of bone removal required to anchor bone plate 10 and preserving the blood supply throughout the fracture site. The channel 66 may be of uniform depth extending from proximal end 62 to distal end 64, or preferably the depth of channel 64 may vary, increasing from proximal end 62 to distal end 64 so that the thickness of the blade portion in the channel is greatest at the proximal end 62. Blade portion 14 preferably has two channels 66 formed by side walls 69 and central wall 70. Although FIG. 13 shows two channels 66 included in blade portion 14, any number of channels may be provided as are needed and as are possible across the width of blade portion 14.

As shown in FIG. 3, blade portion 14 may also include a cannulation or bore 68 running from proximal end 62 to distal end 64. The bore 68 preferably is located in the central wall 70. Bore 68 may be dimensioned and configured to receive a guide wire therethrough. In some surgical procedures, it may be desirable to precisely locate blade portion 14 by using a guide wire planted in the bone F at the desired point of insertion. Preferably, the space for the blade portion 14 is prepared by the surgeon using a chisel as known in the art. The blade portion 14 may then be located and placed over the guide wire such that the guide wire is received in the bore 68. The plate 10 may then be anchored to the bone F. Additionally, bone plate 10 may include any where along its length additional bores or cannulations configured and dimensioned to receive guide wires for facilitating location of bone plate 10 along fractured bone F.

Bone plate 10 may be constructed from biocompatible materials such as, for example, titanium, titanium alloys, stainless steel, ceramics, resorbable materials, and allograft, although one of ordinary skill in the art will know and appreciate that any biocompatible material may be used. The bone plate 10 may also be coated with various substances including, for example microbial agents, antibiotics, and/or growth factors including coatings that contain such substances.

Further it should be understood that variations and modifications within the spirit and scope of the invention may occur to those skilled in the art to which the invention pertains. Accordingly, all modifications attainable by one versed in the art from the disclosure set forth herein are to be included as further embodiments of the present invention. The scope of the present invention is accordingly defined as set forth in the appended claims.

What is claimed:

1. A bone plate for fixation of a fractured bone, the bone plate comprising:
   a first portion having a first longitudinal axis, an upper surface and a lower surface;
   a second bladed portion having a second longitudinal axis, an upper surface and a lower surface, the second portion being angled with respect to the first portion such that the lower surface of the first portion and the lower surface of the second portion define a first included angle therebetween;
   the first portion having at least one hole for receiving a bone anchor having a shaft, the hole having
      a first hole portion defining a first central axis substantially perpendicular to the lower surface at the at least one hole, the first hole portion being configured to receive the bone anchor; and a second hole portion overlapping and in communication with the first hole portion from upper to lower surface and defining a second central axis angled with respect to the first central axis, at least a portion of the second hole portion being threaded, wherein the second hole portion is configured to receive the bone anchor in a single, predetermined angular position such that the shaft of the bone anchor is substantially coaxial with the second central axis and non-perpendicular to the lower surface of the first portion of the bone plate at the at least one hole.

2. The bone plate of claim 1, wherein the second central axis of the hole is angled so as to substantially intersect the second longitudinal axis of the bone plate at a point below the lower surface of the first portion of the bone plate.

3. The bone plate of claim 1, wherein the first longitudinal axis defines a plane that bisects the first portion of the bone plate and wherein further the second central axis intersects the plane at a single point.

4. The bone plate of claim 1, wherein the angle between the second central axis and the first central axis ranges from about 10° to about 35°.

5. The bone plate of claim 1, wherein the second hole portion is configured to receive the bone anchor such that the shaft is substantially at a fixed angle with respect to the second portion of the bone plate.

6. The bone plate of claim 5, wherein at least a portion of the second hole portion conically tapers from the upper surface toward the lower surface.

7. The bone plate of claim 1, wherein the threaded portion of the second hole portion angularly ranges about 190° to about 280° along a periphery of the second hole portion about the second central axis.

8. The bone plate of claim 1, further comprising a bone anchor having a threaded head received in the second hole portion, the head threadedly engaged with the threaded portion of the second hole portion, the bone anchor being configured and dimensioned so as to contact at least a portion of the second portion of the bone plate.

9. The bone plate of claim 1, wherein the second bladed portion of the bone plate is configured and adapted to be inserted within the interior of the fractured bone.

10. The bone plate of claim 9, wherein the upper surface of the blade includes at least one channel.

11. The bone plate of claim 9, wherein the blade includes a bore extending from proximal to distal end, the bore being dimensioned and configured to receive a guide wire.

12. The bone plate of claim 1, wherein the first included angle ranges from about 75° to about 110°.

13. The bone plate of claim 1, wherein the first hole portion is smooth and is elongated in the direction of the first longitudinal axis.

14. The bone plate of claim 1, wherein the first hole portion of the at least one hole is elongated in the direction of the first longitudinal axis and includes a first substantially spherical counterbore along the upper surface and a second counterbore along the lower surface of the bone plate, the first hole portion being configured to receive a bone anchor having a spherical head and the first counterbore being configured to engage the spherical head for compression or distraction of the fracture.

15. The bone plate of claim 1, further comprising:

a second hole on the first plate portion, the second hole being threaded and having a central axis A, the second hole further being configured for threadably receiving a bone anchor having a shaft in a predetermined, fixed angular position such that the shaft is substantially aligned along the central axis A; and a third hole on the first plate portion, the third hole being threaded and having a central axis B, the third hole further being configured for threadably receiving a bone anchor having a shaft in another predetermined, fixed angular position such that the shaft is substantially aligned along the second central axis B of the third hole, wherein the central axes A, B are angled relative to the second plate portion, angled relative to one another, and substantially non-perpendicular to the lower surface of the first plate portion at the second and third holes, respectively, such that the central axes A, B intersect the second longitudinal axis of the second plate portion at a point below the lower surface of the first plate portion.

16. A bone plate for fixation of a fractured bone, the bone plate comprising:

an elongated plate portion having a first longitudinal axis, an upper surface and a lower surface;

a blade portion configured to be inserted into the interior of the fractured bone, the blade portion having a second longitudinal axis, an upper surface and a lower surface, the blade portion being angled with respect to the plate portion so as to define an included angle therebetween and the upper surface of the blade portion including a plurality of longitudinal channels;

the plate portion having at least one hole for receiving a bone anchor having a shaft, the hole having a first portion defining a first central axis substantially perpendicular to the lower surface at the at least one hole; and a second portion overlapping and in communication with the first portion from the upper surface to the lower surface and defining a second central axis angled with respect to the blade portion, the second hole portion having a periphery, at least a portion of the periphery being threaded, wherein the second hole portion is configured to threadably receive the bone anchor such that the shaft is substantially coaxially aligned with the second central axis, threadably and angularly fixed in a single, predetermined position with respect to the blade portion and non-perpendicular to the lower surface of the plate portion at the at least one hole.

17. The bone plate of claim 16, wherein the thread periphery of the second hole portion angularly ranges about the second central axis from about 190° to about 280°.

18. The bone plate of claim 16, further comprising a bone anchor in the form of a first bone screw having a threaded shaft and a threaded head, the bone screw received in the second portion of the at least one hole, the threaded shaft being angled with respect to the blade portion so as to form a truss, wherein the threaded head is engaged with the threaded portion of the periphery of the second portion of the at least one hole so as to lock the bone plate with respect to the bone screw.

19. The bone plate of claim 16, wherein at least a portion of the second hole portion conically tapers from the upper surface toward the lower surface.

20. The bone plate of claim 16, wherein the first hole portion of the at least one hole is elongated in the direction of the first longitudinal axis and includes a first substantially spherical counterbore along the upper surface and a second counterbore along the lower surface of the bone plate, the first hole portion being configured to receive a bone anchor having a spherical head and the first counterbore being configured to engage the spherical head for compression or distraction of the fracture.

21. The bone plate of claim 16, wherein the at least one hole is located on the bone plate such that at least one of the first and second central axes is spaced relative to the first longitudinal axis of the elongated plate portion.

22. The bone plate of claim 21, further comprising:
a second bone screw having a spherical head; and
a second hole, the second bone screw received in the second hole, the second hole having a first substantially spherical counterbore along the upper surface and a second counterbore along the lower surface of the bone plate, the second bone screw received in the second hole such that the first substantially spherical counterbore is engaged with the spherical head for compression or distraction of the fracture.

23. A bone plate system comprising:
at least one bone anchor having a shaft and a head portion;
a bone plate having an elongated plate portion having a first longitudinal axis, an upper surface and a lower surface and a blade portion having a second longitudinal axis, an upper surface and a lower surface, the blade portion configured to be inserted into the interior of the fractured bone and being angled with respect to the plate portion so as to define an included angle therebetween ranging between about 75° and about 110°;
the plate portion having at least one hole, the hole having
a first portion defining a first central axis and including a first counterbore along the upper surface, the first hole portion being configured to receive the bone anchor such that the head is capable of sliding engagement with the first counterbore; and
a second hole portion in communication with the first hole portion from the upper surface to the lower surface and defining a second central axis angled with respect to the blade portion and non-perpendicular with respect to the elongated plate portion at the at least one hole, the second hole portion including a second counterbore that is at least partially threaded,
wherein the second hole portion is configured to receive the bone anchor in a single, predetermined angular position such that the shaft is substantially coaxially aligned with the second central axis and the head portion is fixedly engaged with the second counterbore.

24. The bone plate system of claim 23, wherein a head portion of at least one bone anchor is threaded, and the second counterbore being is configured for fixed threaded engagement with the head portion of the bone anchor.

25. The bone plate system of claim 23, wherein at least one of the first and second central axes is spaced relative to the first longitudinal axis.

26. The bone plate of claim 23, wherein the upper surface of the blade portion includes at least one channel.

27. The bone plate of claim 23, wherein the blade portion includes a bore extending from proximal to distal end, the bore being dimensioned and configured to receive a guide wire.

28. The bone plate of claim 23, wherein the bone anchor is inserted through the second hole portion and angled with respect to the blade portion so as to form a truss, the bone anchor of such a length that at least a portion of the bone anchor contacts the blade portion of the bone plate.

29. The bone plate of claim 23, further comprising:
a second hole on the plate portion, the second hole being threaded and having a central axis A, the second hole further being configured for threadably receiving a second bone anchor having a shaft in a predetermined, fixed angular position such that the shaft is substantially aligned along the central axis A; and
a third hole on the first plate portion, the third hole being threaded and having a central axis B, the third hole further being configured for threadably receiving a third bone anchor having a shaft in another predetermined, fixed angular position such that the shaft is substantially aligned along the second central axis B of the third hole,
wherein the central axes A, B are angled relative to the blade portion, angled relative to one another, and substantially non-perpendicular to the lower surface of the plate portion at the second and third holes, respectively, such that the central axes A, B intersect the second longitudinal axis of the blade portion at a point below the lower surface of the plate portion.

30. A bone plate for fixation of a fractured bone, the bone plate comprising:
an elongated plate portion having a first longitudinal axis, an upper surface and a lower surface and a blade portion having a second longitudinal axis, an upper surface and a lower surface, the blade portion angled with respect to the plate portion;
at least one hole in the plate portion for receiving a bone anchor having a shaft, the hole having
a first hole portion defining a first central axis substantially perpendicular to the lower surface at the at least one hole, the first hole portion being configured to receive the bone anchor; and
a second hole portion overlapping and in communication with the first hole portion from upper to lower surface and defining a second central axis angled with respect to the first central axis, at least a portion of the second hole portion being threaded,
wherein the second hole portion is configured to receive the bone anchor in a single, predetermined angular position such that the shaft of the bone anchor is substantially coaxial with the second central axis and non-perpendicular to the lower surface of the plate portion at the at least one hole.

31. The bone plate of claim 30, wherein the first hole portion is substantially smooth.

32. The bone plate of claim 30, wherein the angle between the first central axis and the second central axis ranges from about 10° to about 35°.

* * * * *